(12) United States Patent
Okuda et al.

(10) Patent No.: US 7,497,121 B2
(45) Date of Patent: Mar. 3, 2009

(54) ULTRASONIC SENSOR

(75) Inventors: Yasuyuki Okuda, Aichi-gun (JP);
Takahiko Yoshida, Okazaki (JP);
Makiko Sugiura, Hekinan (JP);
Ryonosuke Tera, Obu (JP); Yuta Hasebe, Obu (JP)

(73) Assignee: DENSO CORPORATION, Kariya (JP)

( * ) Notice: Subject to any disclaimer, the term of this patent is extended or adjusted under 35 U.S.C. 154(b) by 283 days.

(21) Appl. No.: 11/602,262

(22) Filed: Nov. 21, 2006

(65) Prior Publication Data
US 2007/0144261 A1 Jun. 28, 2007

(30) Foreign Application Priority Data
Dec. 22, 2005 (JP) ............................. 2005-369913

(51) Int. Cl.
*G01S 15/93* (2006.01)
(52) U.S. Cl. .......................... 73/632; 310/322; 367/909
(58) Field of Classification Search .................. 73/632; 310/322, 324, 334; 367/909
See application file for complete search history.

(56) References Cited

U.S. PATENT DOCUMENTS 5,381,386 A 1/1995 Lum et al.

FOREIGN PATENT DOCUMENTS

| JP | A-07-055919 | 3/1995 |
| JP | A-2002-058097 | 2/2002 |
| JP | A-2006-140956 | 6/2006 |
| WO | WO 95/02237 | 1/1995 |

OTHER PUBLICATIONS

Notice of Preliminary Rejection Dec. 14, 2007 in corresponding Korean Patent Application No. 10-2006-0119994 (and English Translation).
Kuratli, C. and Qiuting Huang, *A CMOS Ultrasound Range-Finder Microsystem*, IEEE Journal of Solid-State Circuits, vol. 35, No. 12, Dec. 2000, p. 2005-2017.
Office Action dated Mar. 5, 2008 in corresponding German Patent Application No. 10 2006 061 182.9-35 (and English translation).

*Primary Examiner*—John E Chapman
(74) *Attorney, Agent, or Firm*—Posz Law Group, PLC (57) ABSTRACT

An ultrasonic sensor includes a sending element for sending an ultrasonic wave to an object to be detected, a receiving portion for receiving the ultrasonic wave reflected by the object, an oscillating portion that oscillates by the ultrasonic wave transmitted thereto, and a supporting portion for holding an end part of the oscillating portion. The receiving portion is exposed to a space where the object exists. The receiving portion and the oscillating portion are connected through the supporting portion such that the ultrasonic wave received by the receiving portion is transmitted to the oscillating portion through the supporting portion. The oscillating portion is separate from the receiving portion by the supporting portion.

22 Claims, 7 Drawing Sheets

ULTRASONIC SENSOR

CROSS REFERENCE TO RELATED APPLICATION

This application is based on Japanese Patent Application No. 2005-369913 filed on Dec. 22, 2005, the disclosure of which is incorporated herein by reference in its entirety.

BACKGROUND OF THE INVENTION

1. Field of the Invention

The present invention relates to an ultrasonic sensor for detecting an object. For example, a sending element sends ultrasonic waves to an object, the object reflects the ultrasonic waves, and a receiving element in an ultrasonic sensor receives the reflected ultrasonic waves.

2. Description of Related Art

An ultrasonic sensor is mounted to an automobile, and a two-way transmittable element in the sensor sends ultrasonic waves to an object. The object reflects the waves, and the two-way transmittable element receives the reflected waves. Thus, a position or a distance for the object around the automobile can be measured. Further, a two-dimensional shape or a three-dimensional shape of the object can be measured. That is, the ultrasonic sensor is used for a safe driving by monitoring surroundings of the automobile.

For example, an automatic parking supporting system using an ultrasonic sensor is practically used. In the system, a back-sonar is used for detecting a human or an obstacle existing in the back of an automobile. The ultrasonic sensor is mounted to a rear part of the automobile, and receives ultrasonic waves reflected by the human or the obstacle. Thus, a back side collision with the human or the obstacle can be reduced.

Further, by using a micro electro mechanical system (MEMS) technology, an oscillating portion made of a piezoelectric membrane is formed on a membrane portion in a substrate, as an element for an ultrasonic sensor. Here, when the element is mounted to an automobile in an exposed state, a distance to an object to be detected may not accurately be measured, because water drops or dust may easily adhere onto a surface of the element. Moreover, the element may be damaged and destroyed by a load of an external force, e.g., a collision with a small stone.

JP-A-2002-58097 discloses an ultrasonic sensor having a protective construction for reducing the adhesion and the destruction. In the sensor, a piezoelectric element for detecting ultrasonic waves is disposed in an aluminum case so as not to be exposed to an outside. The piezoelectric element is directly mounted to an oscillating board, and the sensor receives the waves by oscillations of the oscillating board.

However, a mechanical strength of the piezoelectric membrane as the element produced by the MEMS technology is low due to its structure. When the element is directly mounted to the oscillating board, the element may easily be destroyed. By contrast, if a space is provided between the piezoelectric membrane and the oscillating board in order to reduce the destruction, the waves may not effectively be transmitted to the element.

Furthermore, when a resonance oscillation of a receiving portion is used for transmission of ultrasonic waves, a thickness of an oscillating board is determined by a size and a material of the receiving portion, and a frequency of the ultrasonic waves. Therefore, when an ultrasonic sensor includes a small element, an oscillating board in the small element has to be thin. For example, if a wave frequency is 50 kHz, and if an aluminum square board, 3 mm on a side, is used as the receiving portion, a thickness of the board has to be equal to or less than 0.1 mm. In this case, strength of the board cannot be secured. If the thickness is increased in order to secure the strength, a signal intensity may be too low to be detected, because an amplitude of an oscillation becomes small.

SUMMARY OF THE INVENTION

In view of the foregoing and other problems, it is an object of the present invention to provide an ultrasonic sensor. According to the ultrasonic sensor, an oscillating portion of an ultrasonic element can be protected, and ultrasonic waves reflected by an object to be detected can effectively be transmitted to the ultrasonic element.

According to an example of the present invention, an ultrasonic sensor includes a sending element for sending an ultrasonic wave to an object to be detected, a receiving portion for receiving the ultrasonic wave reflected by the object, an oscillating portion that oscillates by the ultrasonic wave transmitted thereto, and a supporting portion for holding an end part of the oscillating portion. The receiving portion is exposed to a space where the object exists. The receiving portion and the oscillating portion are connected through the supporting portion such that the ultrasonic wave received by the receiving portion is transmitted to the oscillating portion through the supporting portion. The oscillating portion is separate from the receiving portion by the supporting portion. The oscillating portion and the receiving portion are connected in a non-contact state by the supporting portion.

Accordingly, an oscillating portion of an ultrasonic element can be protected, and ultrasonic waves reflected by an object to be detected can effectively be transmitted to the ultrasonic element.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF PREFERRED EMBODIMENTS

First Embodiment

Figure 1:
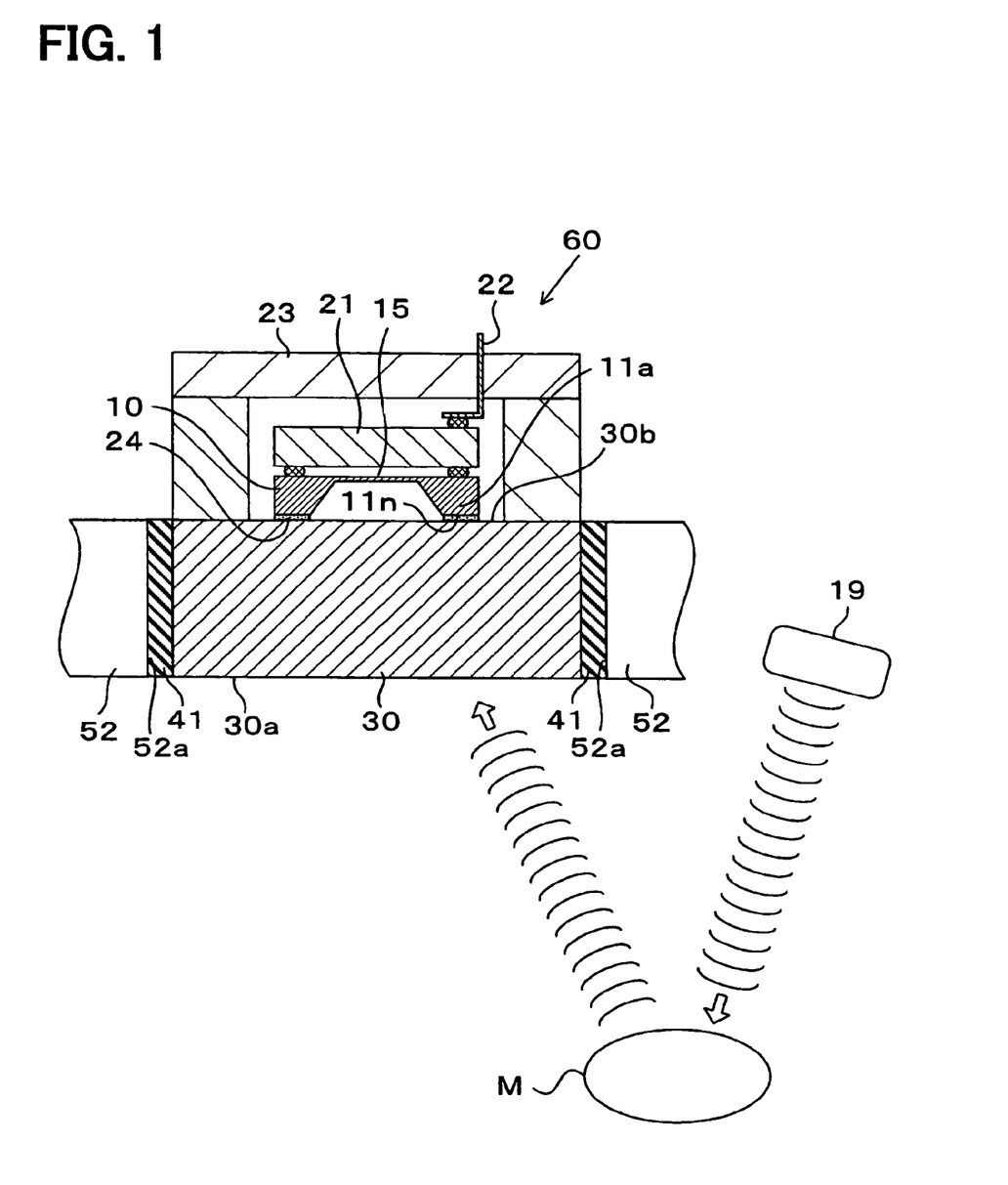
FIG. 1 is a schematic cross-sectional view showing an ultrasonic sensor mounted to an automobile according to an example of a first embodiment.

An ultrasonic sensor 60 is mounted to an automobile, and used for an obstacle detecting sensor in a first embodiment. A lower side of FIG. 1 corresponds to an outside of the automobile. As shown in FIG. 1, a sending element 19 sends ultrasonic waves to an object, e.g., obstacle M, to be detected around the automobile. Then, the waves are reflected by the obstacle M, and the reflected waves are received by a receiving portion 30. The receiving portion 30 is formed into a quadrangular board, and mounted to a bumper 52 of the automobile such that a receiving part 30a for receiving the waves is exposed to the outside of the automobile. The bumper 52 has a mounting portion 52a, and the mounting portion 52a has a hole, into which the receiving portion 30 is inserted. The receiving portion 30 is mounted to the mounting portion 52a through a buffering portion 41 for reducing transmission of the ultrasonic waves.

A receiving element 10 has a supporting part 11a, and a mounting face 11n of the supporting part 11a is mounted to an inner face 30b of the receiving portion 30 through a connecting layer 24. The receiving element 10 is disposed in a box-shaped casing 23 so as not to be exposed to the outside of the automobile. That is, the receiving element 10 is mounted to the receiving portion 30 through the supporting part 11a such that an oscillating portion 15 and the receiving portion 30 are not in contact with each other. The oscillating portion 15 is separate from the receiving portion 30 by the supporting part 11a.

Figure 2A:
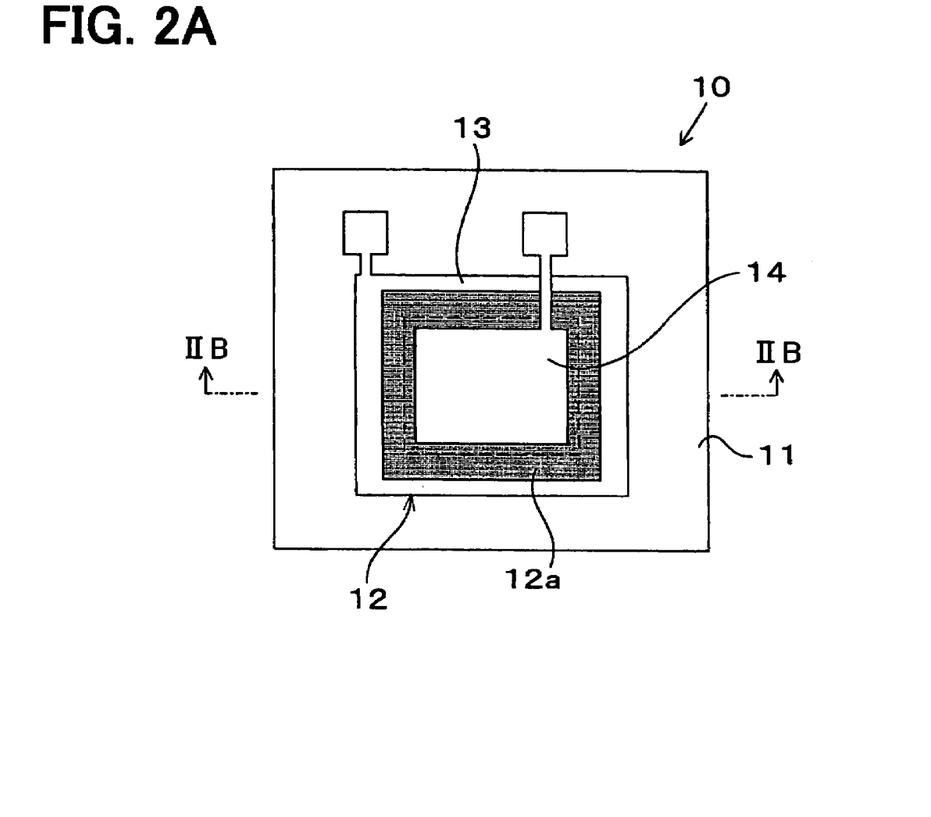
FIG. 2A is a plan view showing a receiving element for the ultrasonic sensor according to the first embodiment.
Figure 2B:
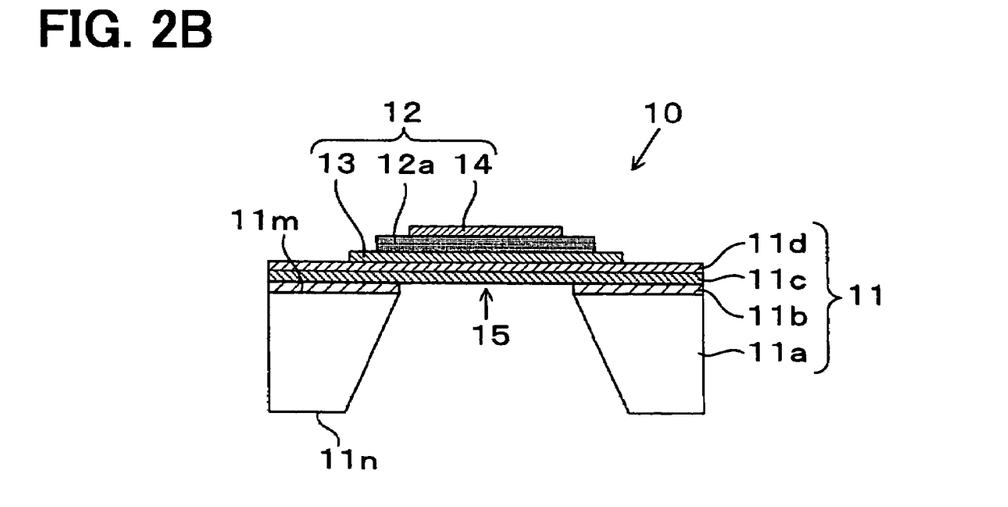
FIG. 2B is a cross-sectional view taken along line IIB-IIB in FIG. 2A.

A circuit element 21 for detecting a voltage signal output from a piezoelectric oscillation detecting element 12 shown in FIGS. 2A and 2B is electrically connected to the receiving element 10. A terminal 22 for inputting the signal into an electronic control unit (ECU, not shown) is electrically connected to the circuit element 21. The terminal 22 is exposed from the casing 23, and electrically connected to the ECU. The circuit element 21 may be disposed outside of the casing 23.

As shown in FIGS. 2A and 2B, the receiving element 10 is formed with a quadrangular semiconductor substrate 11 having a silicon on insulator (SOI) structure. The substrate 11 is formed by layering a first insulating film 11b, a silicon active layer 11c and a second insulating film 11d in this order on a top face 11m of the supporting part 11a. Approximately center parts of the supporting part 11a and the first insulating film 11b are removed in a quadrangular shape by using a micro electro mechanical system (MEMS) technology, as shown in FIG. 2B. Thus, the supporting part 11a is formed into a board shape, and approximately center parts of the supporting part 11a and the first insulating film 11b are removed in a quadrangular shape, such that the silicon active layer 11c and the second insulating film 11d are left in a quadrangular membrane shape.

The detecting element 12 is formed on the second insulating film 11d so as to cover the membrane shape. The detecting element 12 is formed by sandwiching a piezoelectric membrane 12a between a bottom electrode 13 and a top electrode 14. For example, the membrane 12a is made of lead zirconate titanate (PZT). Thus, the oscillating portion 15 can be formed, ends of which are held by the supporting part 11a. The oscillating portion 15 has a predetermined resonance frequency, and resonates with ultrasonic waves transmitted to the receiving element 10. A displacement of the oscillating portion 15 due to the resonance is transformed into a voltage signal by the detecting element 12. Thereby, the ultrasonic waves can be detected. The receiving element 10 formed by using the MEMS technology is useful, because the element 10 is highly sensitive to the ultrasonic waves.

As shown in FIG. 1, ultrasonic waves sent from the sending element 19 are reflected by the obstacle M, and received by the receiving part 30a of the receiving portion 30. The received waves are transmitted toward the receiving element 10 in a thickness direction of the receiving portion 30. Then, the waves are transmitted from the inner face 30b through the connecting layer 24 to the mounting face 11n of the supporting part 11a as a solid-interior oscillation, i.e., compression wave. The waves are transmitted through the supporting part 11a, and the oscillating portion 15 oscillates with the waves. Then, by the oscillation of the oscillating portion 15, the detecting element 12 outputs a voltage signal to the circuit element 21. Accordingly, in the ultrasonic sensor 60, waves received by the receiving portion 30 can be transmitted to the oscillating portion 15 through the supporting part 11a.

The circuit element 21 performs a calculation based on the voltage signal output from the detecting element 12. For example, the signal is amplified, or noises in the signal are removed. Further, a time difference or a phase difference can be calculated by comparing waves received by the receiving element 10 and waves sent from the sending element 19. Thereby, a distance between the obstacle M and the automobile can be measured.

A transmitting rate T represents a ratio of an oscillation intensity transmitted to the oscillating portion 15 to an ultrasonic wave intensity received by the receiving part 30a. The receiving portion 30 absorbs energy of an ultrasonic wave with a transmitting rate T1. An ultrasonic wave is reflected, i.e., not transmitted, by an interface between the receiving portion 30 and the supporting part 11a with a transmitting rate T2. An ultrasonic wave is transmitted through the supporting part 11a having a minimum cross-sectional area Dmin with a transmitting rate T3. The transmitting rate T can be expressed by the transmitting rates T1, T2 and T3 in Formula 1.

$$T1 = T1 \times T2 \times T3 \quad \text{(Formula 1)}$$

Here, in the ultrasonic sensor 60, in order to accurately output a voltage signal to the circuit element 21 based on an oscillation transmitted to the oscillating portion 15, a signal having an intensity equal to or more than a tenth of an intensity received by the receiving part 30a is transmitted to the oscillating portion 15. That is, the transmitting rates T1, T2 and T3 are adjusted such that the transmitting rate T can be equal to or more than 0.1.

The transmitting rate T1 can be expressed by a wave absorbing rate a of a material forming the receiving portion 30 and a thickness TH of the receiving portion 30 in Formula 2.

$$T1 = 1 - \alpha \times TH \quad \text{(Formula 2)}$$

That is, the receiving portion 30 can be formed by a rigid material, which is thin and has a low wave absorbing rate, for example. Further, because the receiving portion 30 is exposed to outside air, the receiving portion 30 is formed by a weatherproof robust material so as to be protected from a load of an external force.

The transmitting rate T2 can be expressed by an acoustic impedance Z1 of the receiving portion 30 and an acoustic impedance Z2 of the supporting part 11a in Formula 3.

$$T2=4\times Z1\times Z2/(Z1+Z2)/(Z1+Z2) \quad \text{(Formula 3)}$$

That is, in order to efficiently transmit ultrasonic waves to the receiving element 10, the acoustic impedances Z1, Z2 are made the same or approximately the same. Based on the above reasons, the receiving portion 30 is made of a metal material, e.g., stainless or aluminum alloy. Alternatively, resin, glass, ceramics or rubber may be used for forming the receiving portion 30.

The transmitting rate T3 can be expressed by the minimum cross-sectional area Dmin of the supporting part 11a and an area S of the oscillating portion 15 in Formula 4.

$$T3=Dmin/S \quad \text{(Formula 4)}$$

Formula 4 is effective only when a value for Dmin/S is not large. Formula 4 is effective when the value is equal to or less than 0.5, for example. An effective range for Formula 4 depends on a structure of the receiving element 10. Because the transmitting rates T1, T2 are equal to or less than one, the transmitting rate T3 is at least equal to or more than 0.1 based on Formula 1. That is, an area of the mounting face 11n is equal to or more than a tenth of the area S of the oscillating portion 15 ($\geq$0.1S). Further, a cross-sectional area of the supporting part 11a parallel to the mounting face 11n is equal to or more than a tenth of the area S of the oscillating portion 15 ($\geq$0.1S).

When the oscillating portion 15 resonates with ultrasonic waves received by the receiving part 30a, a transmitted oscillation can be amplified. The resonance oscillation can be determined by a material, an area, a thickness and a shape of the oscillating portion 15. The resonance of the oscillating portion 15 can be designed by these parameters. Further, a signal intensity can be increased, when a thickness of the receiving portion 30 in a wave transmitted direction is made to be an integral multiple of a fourth wavelength. This is because ultrasonic waves can resonate in harmony in the receiving portion 30.

Because the receiving portion 30 is fixed to the bumper 52 through the buffering portion 41 for reducing transmission of ultrasonic waves, lateral transmission of oscillations can be shielded between the receiving portion 30 and the bumper 52. Thus, a sensitivity of the ultrasonic sensor 60 can be improved, because affect of noises can be reduced. In order to obtain this effect, the buffering portion 41 is made of a material having a high oscillation-shielding performance, such as a rubber.

Wave attenuation is caused by reflections on an interface between the inner face 30b and the mounting face 11n. In order to effectively transmit oscillations of ultrasonic waves from the inner face 30b to the mounting face 11n, the attenuation is made to be small. Therefore, the inner face 30b and the mounting face 11n are connected through a material having a low oscillation-attenuating performance, in order to make a contact state between the inner face 30b and the mounting face 11n better. For example, a grease, a glass jointed layer, an adhesive or a braze is used for the connecting layer 24 such that the inner face 30b and the mounting face 11n can be in a close contact with each other. Further, the inner face 30b and the mounting face 11n may be formed to have flat and smooth surfaces, and made in a mechanical contact. Accordingly, oscillations of ultrasonic waves can efficiently be transmitted from the inner face 30b of the receiving portion 30 to the mounting face 11n of the supporting part, 11a.

Figure 3:
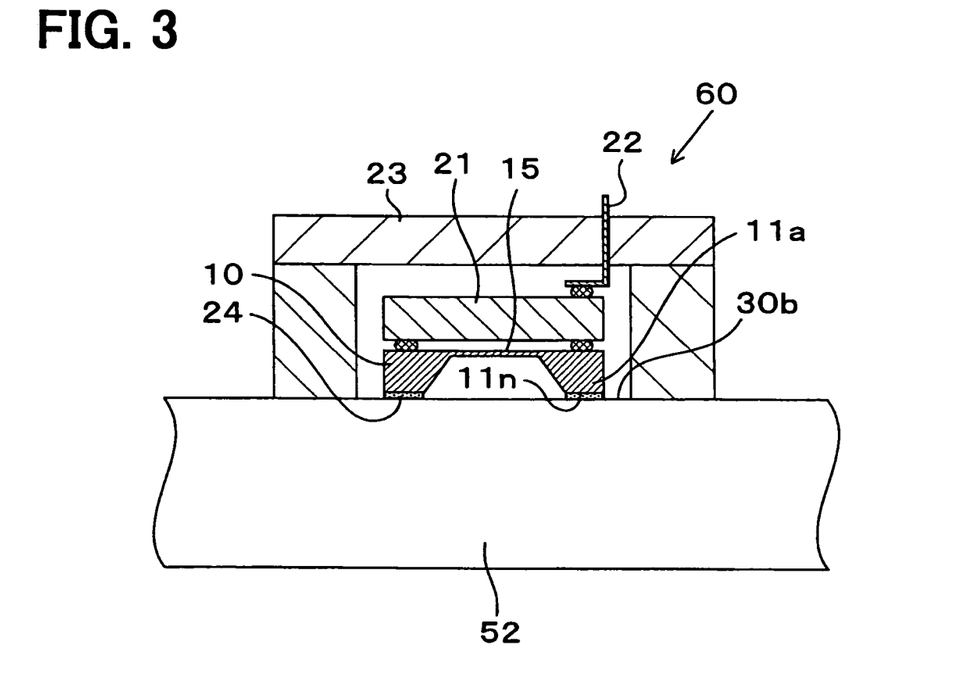
FIG. 3 is a schematic cross-sectional view showing an ultrasonic sensor according to another example of the first embodiment.

FIG. 3 shows an another example of the first embodiment. As shown in FIG. 3, the bumper 52 made of resin or metal may be used as the receiving portion 30, and the receiving element 10 may be directly mounted to the bumper 52 without using the receiving portion 30 in FIG. 1. In this case, because the receiving part 30a is not exposed from the bumper 52, an automobile having a high-quality design can be obtained.

The ultrasonic sensor 60 may be mounted to an end portion of an automobile in a driving direction other than the bumper 52. The sensor 60 may be mounted to a body of the automobile, for example, to a body directly above or beneath the bumper 52. In this case, because ultrasonic waves reflected by the obstacle M are not blocked by a part of the automobile, the sensor 60 can accurately detect the waves. Accordingly, the sensor 60 can effectively be used for an obstacle sensor.

Moreover, a front glass or a rear glass may be used for the receiving portion 30, and the receiving element 10 may be mounted to the glass. In this case, because the receiving portion 30 is made of a hard glass, a transmitting efficiency for ultrasonic waves can be improved.

Furthermore, other parts of the automobile may be used for the receiving portion 30 based on a usage of the sensor 60. For example, a cover of a winker may be used for the receiving portion 30, and the receiving element 10 may be mounted to the cover, when the sensor 60 is used for an obstacle sensor disposed at a side of the automobile. Also, a cover of a head light, a rear light or a back light, or a body of the automobile may be used as the receiving portion 30, and the receiving element 10 may be mounted to the cover or the body.

As a material forming the receiving portion 30, an anisotropic material may be used in order to transmit ultrasonic waves in one direction by priority. For example, metal fibers or glass fibers are arranged in a resin in a thickness direction of the receiving portion 30. In this case, because a transmitting direction of ultrasonic waves is limited to the thickness direction, dissipation of the waves in a surface direction can be reduced. Thus, attenuation of the waves can be reduced.

According to the example of FIG. 1 of the first embodiment, ultrasonic waves sent from the sending element 19 and reflected by the obstacle M are received by the receiving portion 30 mounted to the bumper 52. The receiving part 30a of the receiving portion 30 is exposed from the bumper 52 to the obstacle M side. That is, the receiving part 30a is exposed to an outside of the automobile. The waves received by the receiving portion 30 can be transmitted to the oscillating portion 15 through the supporting part 11a. Thus, the waves can be transmitted as oscillations of the solid interior. Therefore, the waves can efficiently be transmitted to the oscillating portion 15, because attenuation of the waves is small. Further, because the transmission is performed not by a resonance of the receiving portion 30 but by the oscillations of the solid interior, a thickness of the receiving portion 30 can be increased. Accordingly, strength of the receiving portion 30 can be secured.

The supporting part 11a is mounted to the inner face 30b such that the oscillating portion 15 and the receiving portion 30 are not in contact with each other. That is, the oscillating portion 15 is separate from the receiving portion 30 to form a space portion therebetween, and the space portion is enlarged from the oscillating portion 15 to the receiving portion 30. Therefore, even if the receiving portion 30 is displaced toward the oscillating portion 15 due to a collision with a small stone in a driving, the oscillating portion 15 is not damaged and destroyed by a contact with the receiving portion 30.

Further, even when raindrops and dusts adhere onto the automobile, the oscillating portion 15 is not covered with the raindrops and the dusts. Therefore, the ultrasonic sensor 60 can correctly operate. That is, in the sensor 60, the oscillating portion 15 is protected and waves reflected by the obstacle M are efficiently transmitted to the oscillating portion 15.

Reflections of ultrasonic waves at an interface between the receiving portion 30 and the supporting part 11a can be decreased, because the receiving portion 30 has an acoustic impedance that is equal to or less than an acoustic impedance of the supporting part 11a. Accordingly, transmission efficiency of the waves can be improved.

Amplitude of an oscillation transmitted to the receiving element 10 can be increased, because the oscillating portion 15 resonates with ultrasonic waves received by the receiving part 30a. Accordingly, the waves can efficiently be detected.

The receiving portion 30 is mounted to the mounting portion 52a through the buffering portion 41 for reducing transmission of ultrasonic waves between the receiving portion 30 and the mounting portion 52a. Accordingly, transmission of oscillations from other parts constructing the automobile to the receiving portion 30 can be reduced.

Second Embodiment

Figure 4:
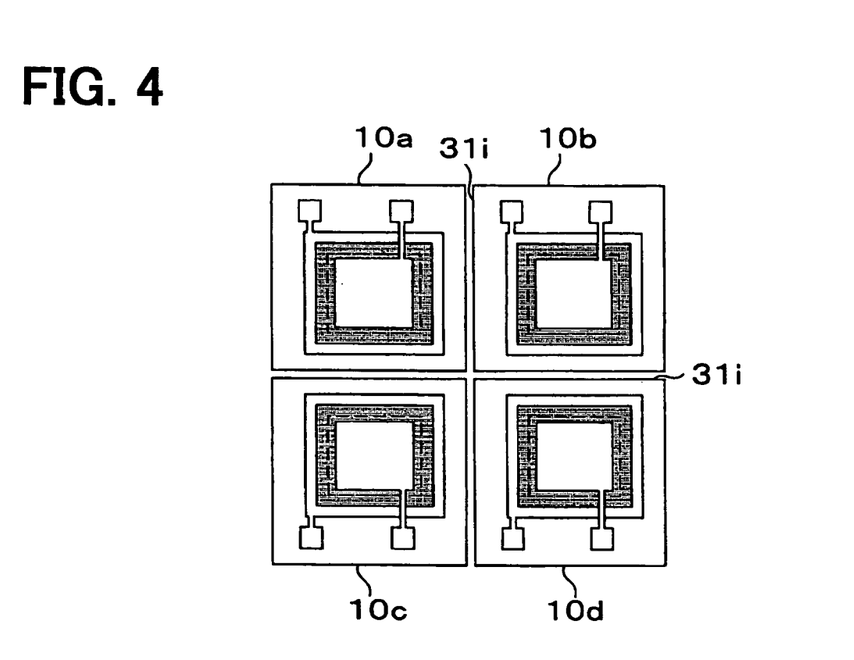
FIG. 4 is a plan view showing receiving elements for an ultrasonic sensor according to a second embodiment.

In an ultrasonic sensor 70 of a second embodiment, plural receiving elements are provided. For example, four receiving elements 10a, 10b, 10c and 10d are disposed in a two-by-two array arrangement, as shown in FIG. 4. Thereby, a time difference and a phase difference can be calculated based on ultrasonic waves received by the receiving elements 10a-10d. Thus, not only a distance but also a position for an object to be detected can be measured based on the differences. A shielding part 31i is provided between the receiving elements 10a-10d adjacent to each other, as shown in FIG. 4. Two of the receiving elements 10a, 10b adjacent to each other have a cross-section shown in FIG. 5, for example.

Figure 5:
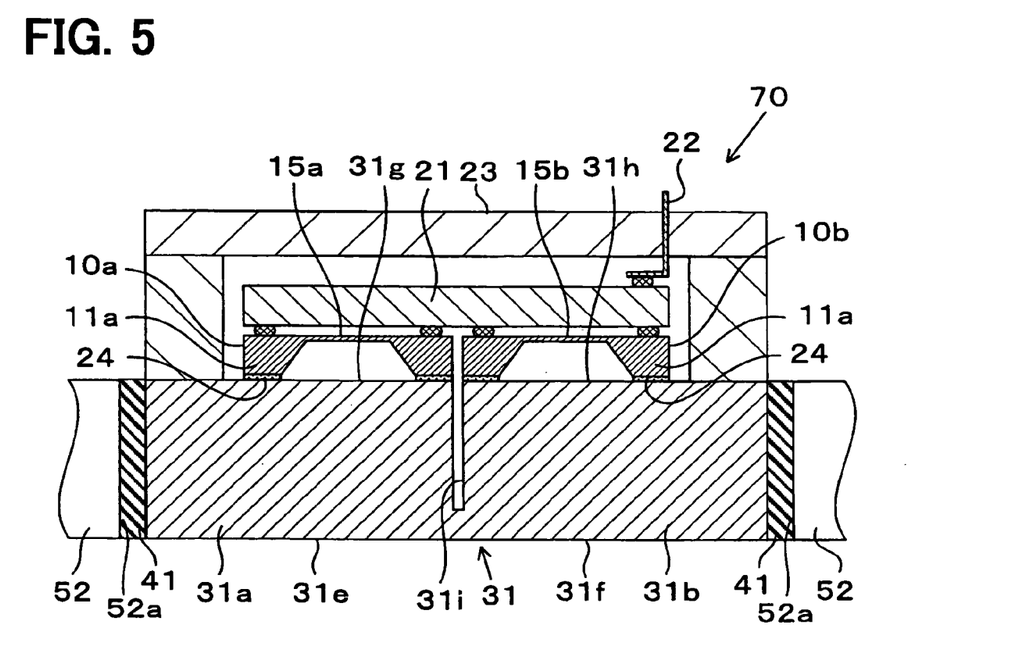
FIG. 5 is a schematic cross-sectional view showing the ultrasonic sensor according to an example of the second embodiment.

As shown in FIG. 5, a receiving portion 31 is mounted to a bumper 52 of an automobile through a buffering portion 41. The receiving portion 31 has the shielding part 31i, and the shielding part 31i is a groove shape. The groove shape of the shielding part 31i is perpendicular to a surface of the receiving portion 31. The shielding part 31i extends from an inner face of the receiving portion 31 toward an outside of the automobile. The receiving portion 31 is divided into areas 31a and 31b by the shielding part 31i. The receiving element 10a is mounted to an inner face 31g of the area 31a, and the receiving element 10b is mounted to an inner face 31h of the area 31b. That is, by the shielding part 31i, the receiving portion 31 is divided into the area 31a corresponding to the receiving element 10a and the area 31b corresponding to the receiving element 10b.

The shielding part 31i has an aperture on the inner face 31g, 31h side and does not have an aperture on a receiving part 31e, 31f side (outside of the automobile). Further, each of the receiving elements 10a, 10b is electrically connected to a circuit portion 21. Furthermore, any two of the elements 10a-10d disposed next to each other have the same cross-sectional construction as the elements 10a, 10b.

In the sensor 70, when the receiving part 31e receives ultrasonic waves, the waves are transmitted through the area 31a. Here, the receiving portion 31 has the shielding part 31i. Therefore, the waves are not transmitted to the area 31b from the area 31a, because attenuation of the waves is large in the shielding part 31i. This is because a transmitting medium in the shielding part 31i is made of air. Accordingly, waves received by the receiving part 31e are transmitted only to an oscillating portion 15a of the receiving element 10a. Similarly, waves received by the receiving part 31f are transmitted only to an oscillating portion 15b of the receiving element 10b. Thereby, transmission of the waves can be performed separately between the areas 31a, 31b. Thus, a cross-talk reduction characteristic for each of the oscillating portions 15a, 15b can be improved. Further, because a time difference and a phase difference of ultrasonic waves received by the receiving parts 31e, 31f can correctly be obtained, accuracy for measuring a position of an obstacle can be improved.

In this embodiment, the shielding part 31i has an aperture on the inner face 31g, 31h side, and does not have an aperture on the receiving part 31e, 31f side. However, the shielding part 31i may not have an aperture on the inner face 31g, 31h side, and have an aperture on the receiving part 31e, 31f side. The shielding part 31i may not have an aperture on both sides of the inner face 31g, 31h and the receiving part 31e, 31f. Further, the shielding part 31i may be provided therein a material for reducing transmission of ultrasonic waves, such as a rubber. The number of the receiving elements is not limited to four. For example, a group of the receiving elements disposed next to each other may be formed, and the shielding part 31i may be provided in every group such that one of the groups is separated from the other groups.

Figure 6:
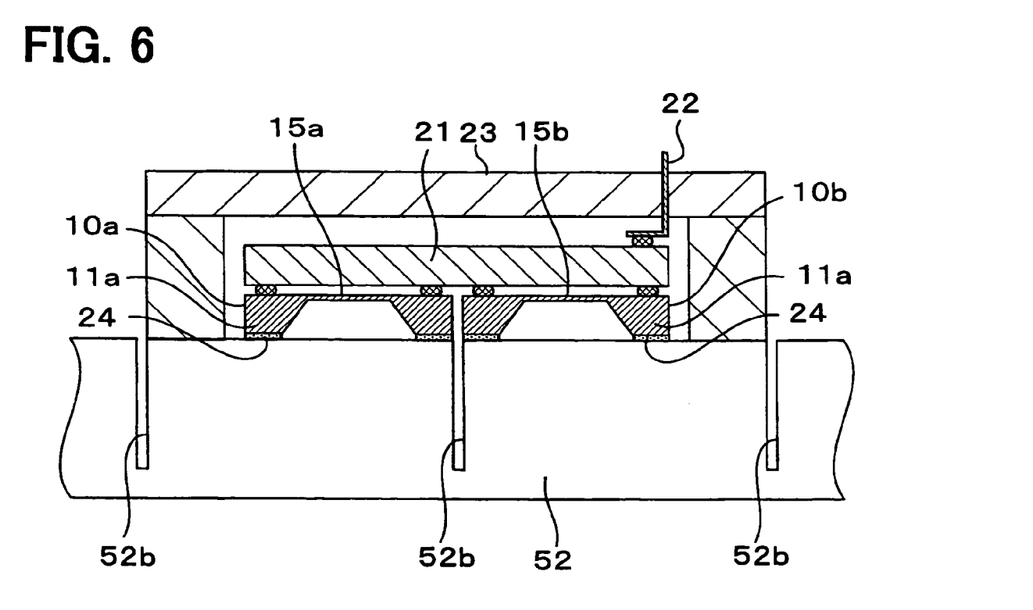
FIG. 6 is a schematic cross-sectional view showing an ultrasonic sensor according to another example of the second embodiment.

As shown in FIG. 6, the bumper 52 may be used as the receiving portion 31, and the receiving elements 10a, 10b may be directly mounted to the bumper 52. Thereby, a looking of the bumper 52 can be made better, because the receiving parts 31e, 31f are not exposed from the bumper 52 to the outside. Here, for example, shielding structures 52b having a similar structure with the shielding part 31i may be provided between the receiving elements 10a, 10b and outside of a casing 23 in a width direction. The structures 52b are provided in the bumper 52 so as to shield transmission of oscillations in a surface direction. Thus, a cross-talk reduction characteristic for each of the oscillating portions 15a, 15b can be improved.

Further, similarly to the first embodiment, a front glass or a rear glass may be used as the receiving portion 31, and the receiving elements 10a-10d may be mounted to the glass. Furthermore, a cover of a head light, a rear light, a back light or a winker, or a body of the automobile may be used as the receiving portion 31, and the receiving elements 10a-10d may be mounted to the cover or the body.

According to the example of FIG. 5 in the second embodiment, the oscillating portions 15a, 15b are mounted to the receiving portion 31 through the supporting part 11a. The receiving portion 31 is divided into the areas 31a, 31b corresponding to the oscillating portions 15a, 15b. The shielding part 31i is disposed between the areas 31a, 31b in order to reduce transmission of ultrasonic waves between the areas 31a, 31b. Thereby, ultrasonic waves received by the area 31a are transmitted only to the oscillating portion 15a, and ultrasonic waves received by the area 31b are transmitted only to the oscillating portion 15b. Therefore, the transmission of the waves can be independently performed between the areas 31a, 31b. Thus, the cross-talk reduction characteristic of each of the oscillating portions 15a, 15b can be improved.

A time difference and a phase difference of ultrasonic waves received by the oscillating portions 15a, 15b can be measured, because the sensor 70 includes the multiple oscillating portions 15a, 15b. Thereby, not only a distance to an obstacle but also a position of the obstacle can be measured based on the differences. Here, ultrasonic waves received by the areas 31a, 31b are transmitted only to the corresponding oscillating portions 15a, 15b. Therefore, the differences can accurately be measured. Accordingly, accuracy for measuring the position of the obstacle can be improved.

Third Embodiment

Figure 7:
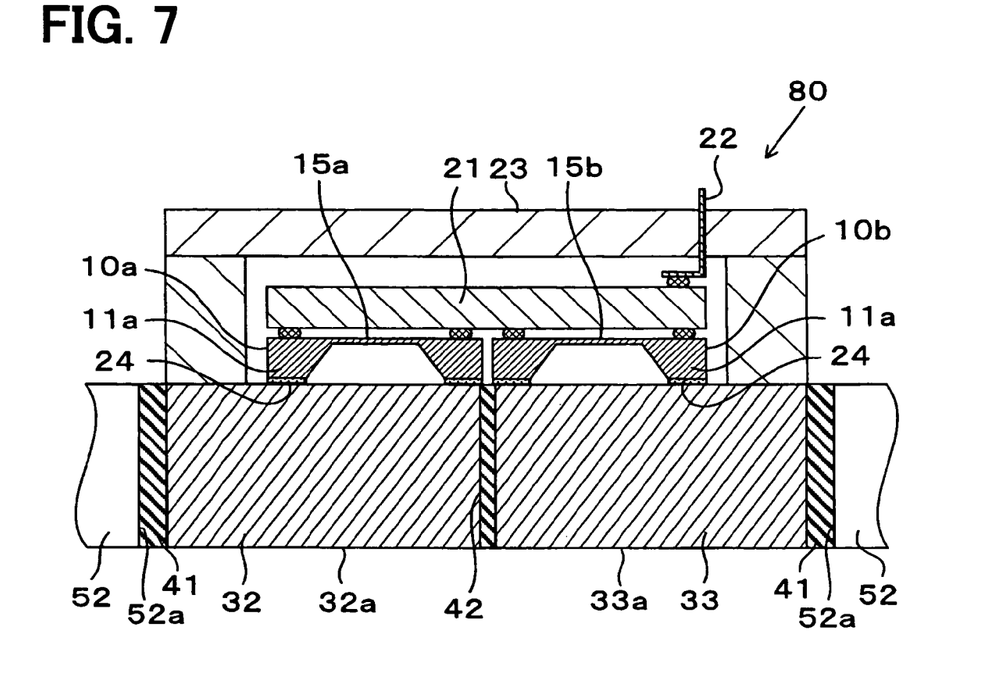
FIG. 7 is a schematic cross-sectional view showing an ultrasonic sensor including multiple receiving elements according to a third embodiment.

As shown in FIG. 7, a receiving portion 32 corresponding to an oscillating portion 15a and a receiving portion 33 corresponding to an oscillating portion 15b are disposed in an ultrasonic sensor 80 in a third embodiment. Each of the oscillating portions 15a, 15b is mounted to the corresponding receiving portion 32, 33 through a supporting part 11a. An attenuating portion 42 made of an attenuating material such as rubber is disposed between the receiving portions 32, 33 so as to reduce transmission of ultrasonic waves therebetween.

When ultrasonic waves are received by a receiving part 32a, the waves are transmitted through the receiving portion 32. Because the attenuating portion 42 is disposed between the receiving portions 32, 33, the waves are difficult to be transmitted from the receiving portion 32 to the receiving portion 33. Therefore, waves received by the receiving part 32a are transmitted only to the oscillating portion 15a of a receiving element 10a. Similarly, waves received by the receiving part 33a are transmitted only to the oscillating portion 15b of a receiving element 10b. Thereby, the transmission of the waves can be separately and independently performed between the receiving portions 32, 33. Thus, a cross-talk reduction characteristic of each of the oscillating portions 15a, 15b can be improved. Further, a time difference and a phase difference can accurately be measured. Accordingly, accuracy for measuring a position of an obstacle can be improved.

According to the third embodiment, each of the oscillating portions 15a, 15b is mounted to the corresponding receiving portion 32, 33 through the supporting part 11a. The attenuating portion 42 is disposed between the receiving portions 32, 33. Therefore, waves received by each of the receiving portions 32, 33 are transmitted only to the corresponding oscillating portion 15a, 15b. Thus, transmission of the waves can be performed separately between the receiving portions 32, 33. Accordingly, a cross-talk reduction characteristic of each of the oscillating portions 15a, 15b can be improved.

The sensor 80 includes the multiple oscillating portions 15a, 15b. Not only a distance but also a position of an obstacle can be measured based on a time difference and a phase difference of waves received by the oscillating portions 15a, 15b. Here, waves received by the receiving portion 32, 33 are transmitted only to the corresponding oscillating portion 15a, 15b. Therefore, the differences can accurately be obtained. Accordingly, accuracy for measuring the position of the obstacle can be improved.

OTHER EMBODIMENTS

Figure 8A:
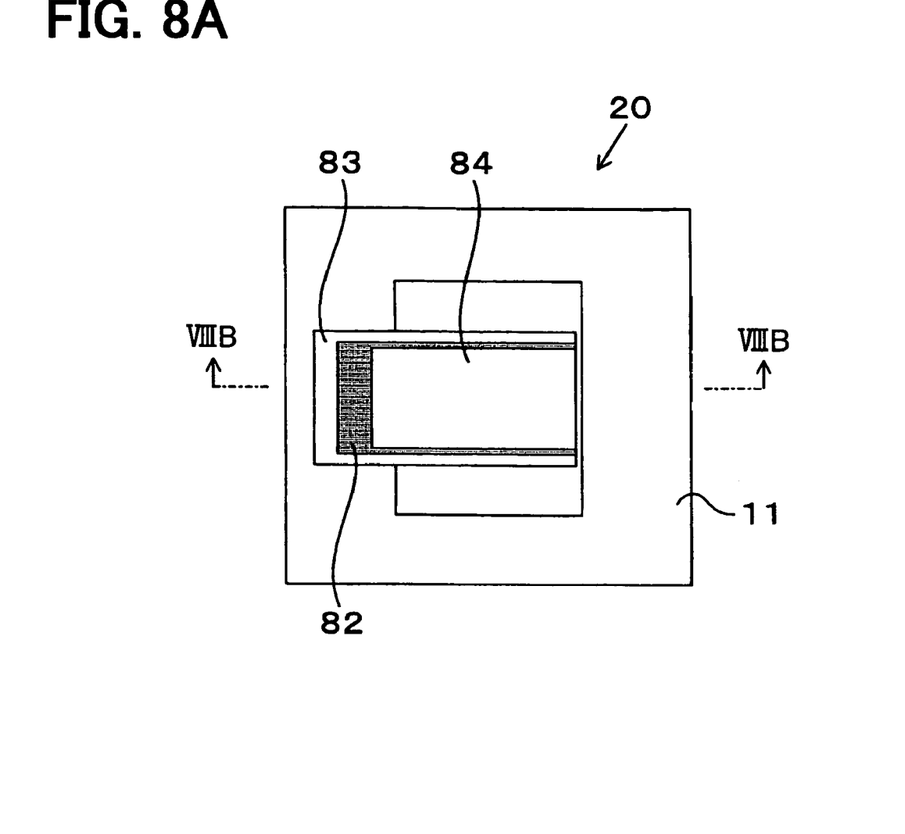
FIG. 8A is a plan view showing a receiving element with an oscillating portion cantilevered by a supporting portion according to a modification of the present invention.
Figure 8B:
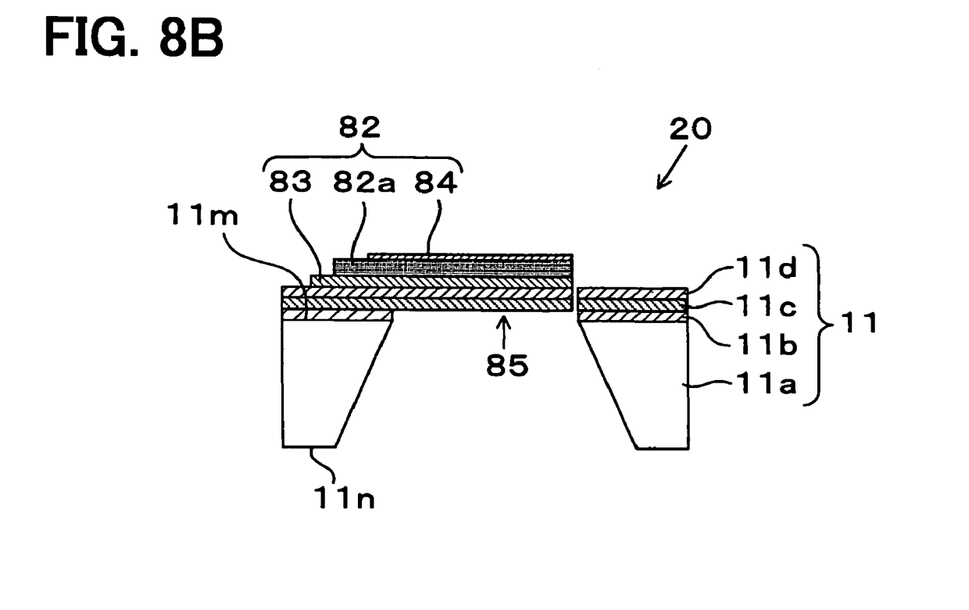
FIG. 8B is a cross-sectional view taken along line VIIIB-VIIIB in FIG. 8A.

As shown in FIGS. 8A and 8B, a receiving element 20 may have an oscillating portion 85 supported at one end by a supporting part 11a. The oscillating portion 85 is formed by layering a silicon active layer 11c, a second insulating film 11d and a piezoelectric oscillation detecting element 82 in this order. The element 82 is formed by sandwiching a piezoelectric membrane 82a between a bottom electrode 83 and a top electrode 84. The oscillating portion 85 is cantilevered by the supporting part 11a.

Figure 9:
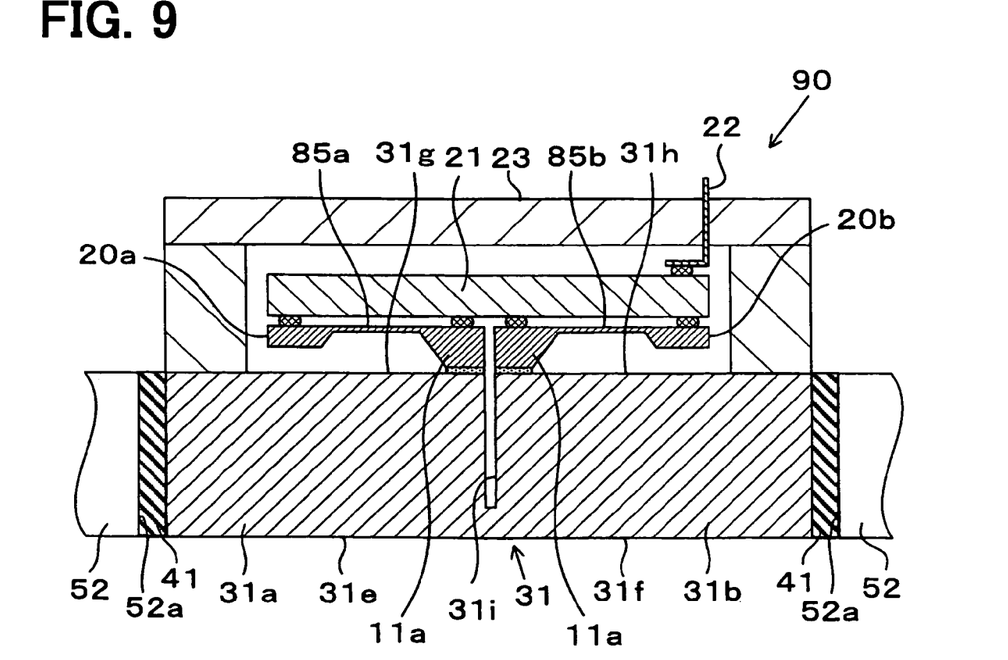
FIG. 9 is a schematic cross-sectional view showing an ultrasonic sensor including receiving elements with an oscillating portion supported at one side by a supporting portion according to another modification of the present invention.

As shown in FIG. 9, when receiving elements 20a, 20b are mounted to a receiving portion 31, a supporting part 11a cantilevering each oscillating portion 85a, 85b may be mounted to an approximately center part of the receiving portion 31 in an ultrasonic sensor 90. Further, the supporting part 11a may be mounted to a peripheral part of the receiving portion 31. Furthermore, the supporting part 11a may be located at the same end side of the receiving elements 20a, 20b. In this case, a sensibility of the ultrasonic sensor 90 may be improved, because displacements of the oscillating portions 85a, 85b are large. This is because a part for restraining the oscillating portion 85a, 85b is small compared with a case in which two ends of the oscillating portion 85a, 85b are supported to the receiving portion 31.

Figure 10:
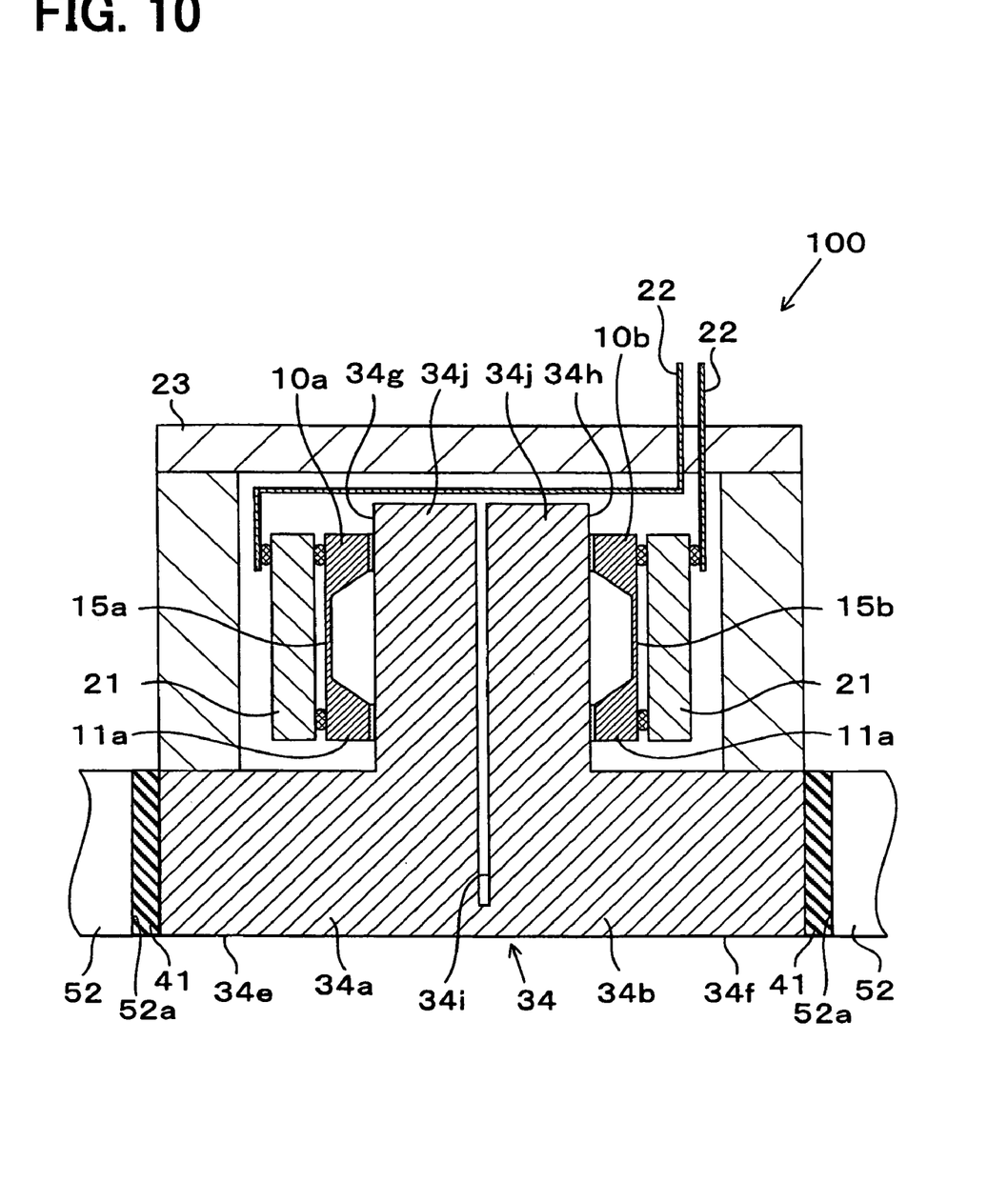
FIG. 10 is a schematic cross-sectional view showing a receiving portion according to a modified example of the present invention.

In FIG. 10, when a wave transmitting time from a receiving part 34e to an oscillating portion 15a of the receiving element 10a and a wave transmitting time from a receiving part 34f to an oscillating portion 15b of the receiving element 10b are the same or approximately the same, accuracy for measuring a time difference of ultrasonic waves can be improved. Thus, accuracy for measuring a position of an obstacle can be improved. For example, a distance from the receiving part 34e corresponding to the receiving element 10a to the oscillating portion 15a and a distance from the receiving part 34f corresponding to the receiving element 10b to the oscillating portion 15b may be made to be the same or approximately the same.

The receiving portions 30-33 may not be a flat shape. As shown in FIG. 10, for example, a protruding part 34j may be formed in a receiving portion 34 of an ultrasonic sensor 100. The protruding part 34j extends from a face opposite to a receiving part 34e, 34f toward an inside of an automobile. A groove-shaped shielding part 34i may be formed at an approximately center part in a width direction of the protruding part 34j. Then, the receiving portion 34 is separated into first and second receiving portions 34a, 34b. Each of the receiving elements 10a, 10b is mounted to a corresponding face 34g, 34h perpendicular to the receiving parts 34e, 34f. The receiving elements 10a, 10b are perpendicular to the receiving parts 34e, 34f. In this embodiment, a circuit element 21 and a terminal 22 may be provided in each of the receiving elements 10a, 10b. In this case, a width of the receiving portion 34 can be made to be small. Therefore, a looking of an automobile can be made better, and flexibility for an arrangement of the sensor 100 can be increased.

The piezoelectric oscillation detecting element 12 is used for the oscillating portion 15 of the receiving element 10 in the example shown in FIGS. 2A and 2B. Alternatively, a capacitance oscillation detecting element may be used for the oscillating portion 15. The capacitance oscillation detecting element can detect ultrasonic waves by a difference of a capacitance between electrodes.

Such changes and modifications are to be understood as being within the scope of the present invention as defined by the appended claims.

What is claimed is:

1. An ultrasonic sensor mounted to a predetermined apparatus, the ultrasonic sensor comprising:
    a sending element for sending an ultrasonic wave to an object to be detected;
    a receiving portion for receiving the ultrasonic wave reflected by the object;
    an oscillating portion which oscillates by the ultrasonic wave transmitted thereto; and
    a supporting portion for holding an end part of the oscillating portion, wherein
    the receiving portion is exposed to a space where the object exists,
    the receiving portion and the oscillating portion are connected through the supporting portion such that the ultrasonic wave received by the receiving portion is transmitted to the oscillating portion through the supporting portion, and the oscillating portion is separate from the receiving portion by the supporting portion.

2. The ultrasonic sensor according to claim 1, wherein:
the receiving portion has an acoustic impedance that is equal to or less than an acoustic impedance of the supporting portion.

3. The ultrasonic sensor according to claim 1, wherein:
the oscillating portion includes a piezoelectric oscillation detecting element.

4. The ultrasonic sensor according to claim 1, wherein:
the oscillating portion is cantilevered by the supporting portion.

5. The ultrasonic sensor according to claim 1, wherein:
the oscillating portion includes a capacitance oscillation detecting element.

6. The ultrasonic sensor according to claim 1, wherein:
the oscillating portion resonates with the ultrasonic wave received by the receiving portion.

7. The ultrasonic sensor according to claim 1, further comprising:
a shielding portion for intercepting a transmission of the ultrasonic wave; wherein
the oscillating portion is one of a plurality of oscillating portions each of which is connected to the receiving portion through the corresponding supporting portion,
the receiving portion is divided into a plurality of receiving areas, each of which corresponds to each of the oscillating portions, and
the shielding portion is provided between the receiving areas.

8. The ultrasonic sensor according to claim 7, wherein:
the shielding portion is a groove-shaped clearance approximately perpendicular to a surface of the receiving portion.

9. The ultrasonic sensor according to claim 1, further comprising:
a shielding portion for intercepting a transmission of the ultrasonic wave; wherein
the oscillating portion is one of a plurality of oscillating portions,
the receiving portion is one of a plurality of receiving portions which correspond, respectively, to the oscillating portions,
each of the oscillating portions is mounted to the corresponding receiving portion through the corresponding supporting portion, and
the shielding portion is provided between the receiving portions.

10. The ultrasonic sensor according to claim 9, wherein:
the shielding portion is made of a material for attenuating the ultrasonic wave.

11. The ultrasonic sensor according to claim 7, wherein:
the receiving portion has a first transmission time, for which an ultrasonic wave received by a first receiving part is transmitted from the first receiving part to the corresponding oscillating portion; and
the first transmission time is equal to or approximately equal to a second transmission time, for which an ultrasonic wave received by a second receiving part is transmitted from the second receiving part to the corresponding oscillating portion.

12. The ultrasonic sensor according to claim 1, wherein:
the predetermined apparatus is an automotive vehicle.

13. The ultrasonic sensor according to claim 12, further comprising:
a mounting shielding portion for intercepting a transmission of the ultrasonic wave; wherein
the automotive vehicle includes a mounting portion for mounting the receiving portion, and
the receiving portion is mounted to the mounting portion through the mounting shielding portion.

14. The ultrasonic sensor according to claim 13, wherein:
the mounting portion is an end portion of the automotive vehicle in a driving direction of the vehicle.

15. The ultrasonic sensor according to claim 13, wherein:
the mounting portion is a bumper of the automotive vehicle.

16. The ultrasonic sensor according to claim 12, wherein:
the receiving portion is disposed at an end portion of the automotive vehicle in a driving direction of the vehicle.

17. The ultrasonic sensor according to claim 12, wherein:
the receiving portion is a bumper of the automotive vehicle.

18. The ultrasonic sensor according to claim 12, wherein:
the receiving portion is at least one of a front glass and a rear glass of the automotive vehicle.

19. The ultrasonic sensor according to claim 12, wherein:
the receiving portion is a cover for at least one of a head light, a rear light, a winker and a back light of the automotive vehicle.

20. The ultrasonic sensor according to claim 12, wherein:
the receiving portion is a body of the automotive vehicle.

21. The ultrasonic sensor according to claim 1, further comprising:
a connecting layer provided between the supporting portion and the receiving portion, for bonding the supporting portion and the receiving portion to each other.

22. The ultrasonic sensor according to claim 1, wherein:
the oscillating portion is separate from the receiving portion to have a space portion therebetween; and
the space portion is enlarged from the oscillating portion to the receiving portion.

* * * * *